United States Patent
Christoph et al.

(10) Patent No.: US 8,536,130 B2
(45) Date of Patent: Sep. 17, 2013

(54) USE OF 1 PHENYL-3-DIMETHYLAMINO-PROPANE COMPOUNDS FOR TREATING NEUROPATHIC PAIN

(75) Inventors: Thomas Christoph, Aachen (DE); Elmar Friderichs, Stolberg (DE); Babette-Yvonne Koegel, Langerwehe-Hamich (DE); Murielle Meen, Ayguesvives (FR)

(73) Assignee: Gruenenthal GmbH, Aachen (DE)

( * ) Notice: Subject to any disclaimer, the term of this patent is extended or adjusted under 35 U.S.C. 154(b) by 195 days.

(21) Appl. No.: 12/850,208

(22) Filed: Aug. 4, 2010

(65) Prior Publication Data

US 2010/0311842 A1    Dec. 9, 2010

Related U.S. Application Data

(63) Continuation of application No. 12/045,830, filed on Mar. 11, 2008, now abandoned.

(60) Provisional application No. 60/906,220, filed on Mar. 12, 2007.

(30) Foreign Application Priority Data

Mar. 12, 2007   (DE) .................. 10 2007 012 165

(51) Int. Cl.
*A61K 38/00*   (2006.01)
*A61K 31/275*   (2006.01)

(52) U.S. Cl.
USPC .......... 514/18.2; 514/529; 514/646; 514/452; 514/456; 514/434

(58) Field of Classification Search
USPC ............... 514/18.2, 529, 646, 452, 456, 434
See application file for complete search history.

(56) References Cited

U.S. PATENT DOCUMENTS 6,248,737 B1   6/2001   Buschmann et al.
6,344,558 B1   2/2002   Buschmann et al.

FOREIGN PATENT DOCUMENTS

| | | |
|---|---|---|
| DE | 44 26 245 A1 | 2/1996 |
| WO | WO 2004/047823 A1 | 6/2004 |
| WO | WO 2007/128413 A1 | 11/2007 |

OTHER PUBLICATIONS

Tzhentke et al., The Journal of Pain, vol. 7, Issue 4, supplemental p. S26, Abstract (687), Apr. 2006.
Dworkin et al., Archives of Neurology, vol. 60, Nov. 2003, pp. 1524-1534.
Tzchentke et al., Drugs of the Future, 2006, vol. 3, Issue 12, p. 1053, Abstract.
Tapentadol Structure Compound 10390, The Merck Index, 14$^{th}$ Edition, 2006, retrieved from Internet on Jan. 29, 2010, URL: http://www.knovel.com/web/portal/basic_search/display.
Christoph et al., *Tapentadol, but not morphine, selectively inhibits disease-related thermal hyperalgesia in a mouse model of diabetic neuropathic pain*, Neuroscience Letters 470 (2010) 91-94.
German Search Report, 4 pages.
International Search Report, 4 pages.
Translation of Written Opinion of the International Searching Authority, 5 pages.
Schwartz, Sherwyn et al., Safety and efficacy of tapentadol ER in patients with painful diabetic peripheral neuropathy: results of a randomized-withdrawal, placebo-controlled trial, Current Medical Research & Opinion, vol. 27, No. 1, 2011, pp. 151-162.
Tzschentke, Thomas et al., Tapentadol HCL: In Vitro and In Vivo Studies on the Dual Mechanism of Action Underlying its Broad Analgesic Profile, American Academy of Pain Medicine, 23$^{rd}$ Annual Meeting, Feb. 7-10, 2007.
Tzscherntke, T. M. et al., Tapendatol Hydrocholoride. In: Drugs Future, 2006, vol. 31, S. 1053-1061; Zusammenf., F. 1056, Tab. III.

*Primary Examiner* — Savitha Rao
(74) *Attorney, Agent, or Firm* — Crowell & Moring LLP

(57) ABSTRACT

Use of 1-phenyl-3-dimethylaminopropane compounds for the production of medicaments for treating neuropathic pain, preferably polyneuropathic pain, also preferably diabetic neuropathic pain, more preferably diabetic peripheral neuropathic pain, and furthermore preferably for treating diabetic peripheral neuropathy.

6 Claims, No Drawings

USE OF 1 PHENYL-3-DIMETHYLAMINO-PROPANE COMPOUNDS FOR TREATING NEUROPATHIC PAIN

CROSS REFERENCE TO RELATED APPLICATIONS

This application is a continuation of application Ser. No. 12/045,830, filed Mar. 11, 2008, now abandoned, which in turn claimed priority from U.S. provisional patent application No. 60/906,220, filed Mar. 12, 2007 and Federal Republic of Germany patent application no. DE 10 2007 012 165.4, filed Mar. 12, 2007, the entire disclosures of which are incorporated herein by reference.

BACKGROUND OF THE INVENTION

The present invention relates to the use of 1-phenyl-3-dimethylaminopropane compounds for the production of medicaments for treating neuropathic, preferably mononeuropathic and/or polyneuropathic pain, particularly preferably polyneuropathic pain, and also preferably diabetic neuropathic pain, preferably diabetic peripheral neuropathic pain, and furthermore preferably for treating diabetic peripheral neuropathy.

The normal physiological pain sensation, which serves as a protective function for the organism, is transmitted via nerve fibres as a response to corresponding painful stimuli. This is referred to as nociceptive pain. This nociceptive pain may be acute or chronic, somatic or visceral, and may be present with or without an inflammatory component. Appropriate stimuli may be mechanical (e.g. pressure), thermal (e.g. heat) or chemical (e.g. acid). Also, electrical stimuli may be perceived as painful.

In contrast to nociceptive pain—and also in most cases not treatable with the same means—neuropathic pain (a non-nociceptive pain; for a review see Hansson et al., 2001 Neuropathic Pain; Pathophysiology and Treatment in Progress in Pain Research and Management, Vol. 21 eds. Hansson et al. IASP Press, Seattle; Bridges et al., 2001 Br J Anaesthesia 87:12-26) is characterized by the occurrence of spontaneous pain and/or pain triggered by abnormal stimuli. Spontaneously occurring pain results for example from so-called ectopic activity of the pain-conducting nerve fibres. In this case the nerve fibre sends a pain signal from the periphery to the central nervous system even though there was no appropriate stimulus. An example of pain that is triggered by an abnormal stimulus is the phenomenon of allodynia. Allodynia is defined as a painful sensation produced by a normally non-painful stimulus. Allodynia is not restricted to neuropathic pain. Thus, allodynia occurs for example in non-neuropathic conditions such as sunburn or arthritis. The underlying mechanisms of allodynia differ however in principle from one another and can be classified by a detailed medical case history and investigation.

A further example of abnormal pain sensation is hyperalgesia. In this case a normally painful stimulus is perceived as producing a more severe pain than would be the case in a healthy situation. This type of increased pain perception occurs not only in neuropathic pain but also for example in inflammatory pain, where however it has a different cause (inflammation) than in neuropathic pain.

Various metabolic diseases may be the cause of neuropathic changes and may subsequently be implicated in neuropathic pain. An example of such a neuropathy is diabetic neuropathy, which occurs in a large number of patients suffering from diabetes mellitus and may be associated with a large number of clinical symptoms such as a feeling of numbness, tingling sensation, or pain. The most common form of diabetic neuropathy is distal symmetrical sensomotor polyneuropathy.

Neuropathic pain occurs inter alia after damage to peripheral or central nerves and can therefore be induced and observed in animal experiments by targeted lesions of individual nerves. Two possible animal models are the nerve lesion according to Bennett (Bennett and Xie, 1988 Pain 33:87-107) as well as that according to Chung (Kim and Chung, 1992 Pain 50:355-363). In the Bennett model the sciatic nerve is bound unilaterally with loose ligatures; in the Chung model two spinal nerves are bound unilaterally. In both cases the development of symptoms of neuropathic pain can be observed and quantified by means of thermal or mechanical allodynia.

A known animal model for investigating diabetic neuropathy is the induction of diabetes in rodents by administration of a single dose of streptozotocin, an antibiotic extract from *Streptomyces acromogenes*, which selectively damages the δ cells of the pancreas. After some time the animals exhibit typical symptoms of diabetic neuropathic pain, such as for example mechanical, thermal or chemical hyperalgesia (Courteix et al., 1993 Pain 53:81-88).

To treat neuropathic pain, among other things, gabapentin is used, which however is relatively ineffective, and then only at significant dosages. On the other hand morphine is also often used, the range of side effects of which are, as is known, not without problems. Against the background of the prior art there was therefore a need for compounds with a favorable ratio of effectiveness to side effects, and to provide compounds for the treatment of neuropathic pain.

SUMMARY OF THE INVENTION

An object of the present invention was accordingly to discover compounds that are effective in treating neuropathic pain, in particular polyneuropathic pain and especially diabetic pain.

A further object of the invention was to provide a new method of effectively treating neuropathic pain without excessive side effects.

The achievement of these objects is complicated by the fact that a large to overwhelming proportion of the substances effective in treating nociceptive pain—such as acute pain—are not effective at all, or are only slightly effective, in treating neuropathic pain.

It has now surprisingly been found that the compounds disclosed hereinbelow are highly effective in treating neuropathic pain, and surprisingly particularly effective in treating polyneuropathic and diabetic neuropathic pain.

Accordingly, the present invention provides for the use of a 1-phenyl-3-dimethylaminopropane compound corresponding to formula I

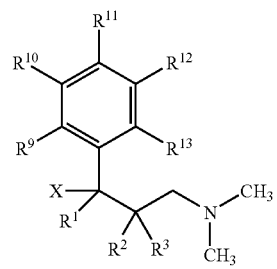

wherein

X is OH, F, Cl, OC(O)CH$_3$ or H, preferably OH, F, OC(O)CH$_3$ or H;

R$^1$ is saturated and unsubstituted, branched or unbranched C$_{1-4}$-alkyl, preferably CH$_3$, C$_2$H$_5$, C$_4$H$_9$ or t-butyl, in particular CH$_3$ or C$_2$H$_5$;

R$^2$ and R$^3$ are independently selected from the group consisting of H and saturated and unsubstituted, branched or unbranched C$_{1-4}$-alkyl; preferably H, CH$_3$, C$_2$H$_5$, i-propyl or t-butyl, in particular H or CH$_3$, especially preferably R$^3$=H; and three or four of R$^9$ to R$^{13}$ correspond to H, and the remainder of R$^9$ to R$^{13}$ are independently selected from the group consisting of H, Cl, F, OH, CF$_2$H, CF$_3$, saturated and unsubstituted, branched or unbranched C$_{1-4}$-alkyl; OR$^{14}$ and SR$^{14}$, wherein R$^{14}$ is saturated and unsubstituted, branched or unbranched C$_{1-3}$-alkyl; preferably the remainder of R$^9$ to R$^{13}$ are independently H, Cl, F, OH, CF$_2$H, CF$_3$, OCH$_3$ or SCH$_3$; or R$^{12}$ and R$^{11}$ form a 3,4-OCH=CH ring, or a pharmaceutically acceptable salt thereof for the treatment of neuropathic pain.

In particular if R$^9$, R$^{11}$ and R$^{13}$ correspond to H, one of R$^{10}$ and R$^{12}$ also corresponds to H, while the other is selected from the group consisting of Cl, F, OH, CF$_2$H, CF$_3$, OR$^{14}$ or SR$^{14}$, preferably OH, CF$_2$H, OCH$_3$ or SCH$_3$; or if R$^9$ and R$^{13}$ correspond to H and R$^{11}$ corresponds to OH, OCH$_3$, Cl or F, preferably to Cl, then one of R$^{10}$ and R$^{12}$ also corresponds to H, while the other corresponds to OH, OCH$_3$, Cl or F, preferably Cl; or if R$^9$, R$^{10}$, R$^{12}$ and R$^{13}$ correspond to H, R$^{11}$ is selected from CF$_3$, CF$_2$H, Cl or F, preferably F; or if R$^{10}$, R$^{11}$ and R$^{12}$ correspond to H, one of R$^9$ and R$^{13}$ also corresponds to H, while the other is selected from OH, OC$_2$H$_5$ or OC$_3$H$_7$.

The compounds optionally may be used in the form of their racemates, their pure stereoisomers, in particular enantiomers or diastereomers, or in the form of mixtures of the stereoisomers, in particular of the enantiomers or diastereomers, in an arbitrary mixture ratio; in the prepared form or in the form of their acids or their bases or in the form of their salts, in particular the physiologically compatible salts, or in the form of their solvates, in particular the hydrates.

The neuropathic pain to be treated may preferably be mononeuropathic and/or polyneuropathic pain, particularly preferably polyneuropathic pain, and furthermore preferably diabetic neuropathic pain, especially preferably diabetic peripheral neuropathic pain. The method of the invention may also preferably be used for treating diabetic neuropathy, and most preferably for treating diabetic peripheral neuropathy.

About 1% of the population suffers from neuropathic pain, in particular polyneuropathic pain, which is one of the most difficult types of pain to treat. There is therefore a need for effective medication for treating in particular diabetic neuropathic pain, especially in patients who are sensitive to the side effects of NSAID analgesics and to μ-opioid agonists, antidepressants and anticonvulsants available on the market, or whose pain cannot be adequately treated with other non-opioid analgesics, antidepressants and anticonvulsants.

Surprisingly it has been found that the aforementioned substances are extremely effective in the two most important in vivo models of neuropathic pain and, what is particularly surprising and should be emphasised, especially in the in vivo model for diabetic neuropathy. The particular selectivity as regards polyneuropathic and diabetic neuropathic pain is shown in further in vivo models (Example 6), and is confirmed by a marked difference in the efficacy (by a factor of 3!). Furthermore, gabapentin was significantly less effective than these compounds.

In particular the present application provides for the use of the substance (1R,2R)-3-(3-dimethylamino-1-ethyl-2-methylpropyl)-phenol, a centrally active analgesic, which has a dual mode of action (μ-opioid receptor agonist and an inhibitor of noradrenaline uptake) coupled with low opioid-typical side effects, in contrast to opioids currently used and available on the market, for the treatment of polyneuropathic, preferably diabetic neuropathic and more particularly diabetic peripheral neuropathic pain.

In the context of the present invention alkyl and cycloalkyl radicals are understood to denote saturated and unsaturated (but not aromatic), branched, unbranched and cyclic hydrocarbons, which may be unsubstituted or monosubstituted or polysubstituted. In this connection C$_{1-2}$-alkyl denotes C1- or C2-alkyl, C$_{1-3}$-alkyl denotes C1-, C2- or C3-alkyl, C$_{1-4}$-alkyl denotes C1-, C2-, C3- or C4-alkyl, C$_{1-5}$-alkyl denotes C1-, C2-, C3-, C4- or C5-alkyl, C$_{1-6}$-alkyl denotes C1-, C2-, C3-, C4-, C5- or C6-alkyl, C$_{1-7}$-alkyl denotes C1-, C2-, C3-, C4-, C5-, C6- or C7-alkyl, C$_{1-8}$-alkyl denotes C1-, C2-, C3-, C4-, C5-, C6-, C7- or C8-alkyl, C$_{1-10}$-alkyl denotes C1-, C2-, C3-, C4-, C5-, C6-, C7-, C8, —C9- or C10-alkyl and C$_{1-18}$-alkyl denotes C1-, C2-, C3-, C4-, C5-, C6-, C7-, C8-, C9-, C10-, C11-, C12-, C13-, C14-, C15-, C16-, C17- or C18-alkyl. In addition C$_{3-4}$-cycloalkyl denotes C3- or C4-cycloalkyl, C$_{3-5}$-cycloalkyl denotes C3-, C4 or C5-cycloalkyl, C$_{3-6}$-cycloalkyl denotes C3-, C4-, C5- or C6-cycloalkyl, C$_{3-7}$-cycloalkyl denotes C3-, C4-, C5-, C6- or C7-cycloalkyl, C$_{3-8}$-cycloalkyl denotes C3-, C4-, C5-, C6-, C7- or C8-cycloalkyl, C$_{4-5}$-cycloalkyl denotes C4- or C5-cycloalkyl, C$_{4-6}$-cycloalkyl denotes C4-, C5- or C6-cycloalkyl, C$_{4-7}$ cycloalkyl denotes C4-, C5-, C6- or C7-cycloalkyl, C$_{5-6}$-cycloalkyl denotes C5- or C6-cycloalkyl and C$_{5-7}$-cycloalkyl denotes C5-, C6- or C7-cycloalkyl. With regard to cycloalkyl the term also includes saturated cycloalkyls in which one or two carbon atoms are replaced by a heteroatom S, N or O. The term cycloalkyl however in addition also includes in particular monounsaturated or polyunsaturated, preferably monounsaturated, cycloalkyls without a heteroatom in the ring, provided that the cycloalkyl does not form an aromatic system. The alky and cycloalkyl radicals are preferably methyl, ethyl, vinyl(ethenyl), propyl, allyl(2-propenyl), 1-propinyl, methylethyl, butyl, 1-methylpropyl, 2-methylpropyl, 1,1-dimethylethyl, pentyl, 1,1-di-methylpropyl, 1,2-dimethylpropyl, 2,2-dimethylpropyl, hexyl, 1-methylpentyl, cyclopropyl, 2-methylcyclopropyl, cyclopropylmethyl, cyclobutyl, cyclopentyl, cyclopentylmethyl, cyclohexyl, cycloheptyl, cyclooctyl, but also adamantyl, CHF$_2$, CF$_3$ or CH$_2$OH as well as pyrazolinone, oxopyrazolinone, [1,4]dioxane or dixolane.

At the same time, in connection with alkyl and cycloalkyl—unless expressly defined otherwise—the term "substituted" within the meaning of the present invention denotes the substitution of at least one (optionally also several) hydrogen atom(s) by F, Cl, Br, I, NH$_2$, SH or OH, in which "polysubstituted" and "substituted" in the case of polysubstitution is understood to mean that the substitution occurs multiply with the same or different substituents on different as well as on the same atoms, for example triple substitution on the same C atom as in the case of CF$_3$, or at different sites, as in the case of —CH(OH)—CH=CH—CHCl$_2$. Particularly preferred substituents in this connection are F, Cl and OH. With regard to cycloalkyl the hydrogen atom may also be replaced by OC$_{1-3}$-alkyl or C$_{1-3}$-alkyl (in each case monosubstituted or polysubstituted, or unsubstituted) in particular by methyl, ethyl, n-propyl, i-propyl, $CF_3$, methoxy or ethoxy.

The term $(CH_2)_{3-6}$ is understood to denote —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$—, the term $(CH_2)_{1-4}$ is understood to denote —$CH_2$—, —$CH_2$—$CH_2$—, —$CH_2$—$CH_2$—$CH_2$— and —$CH_2$—$CH_2$—$CH_2$—$CH_2$—, and similarly the term $(CH_2)_{4-5}$ is understood to denote —$CH_2$—$CH_2$—$CH_2$—$CH_2$— and —$CH_2$—$CH_2$—$CH_2$—$CH_2$—$CH_2$—, etc.

An aryl radical is understood to denote ring systems with at least one aromatic ring, but without heteroatoms in even only one of the rings. Examples are phenyl, naphthyl, fluoranthenyl, fluorenyl, tetralinyl or indanyl, in particular 9H-fluorenyl or anthracenyl radicals, which may be unsubstituted or monosubstituted or polysubstituted.

A heteroaryl radical is understood to denote heterocyclic ring systems with at least one unsaturated ring, which may contain one or more heteroatoms from the group nitrogen, oxygen and/or sulphur and may also be monosubstituted or polysubstituted. Examples of heteroaryl compounds that may be mentioned include furan, benzofuran, thiophene, benzothiophene, pyrrole, pyridine, pyrimidine, pyrazine, quinoline, isoquinoline, phthalazine, benzo[1,2,5]thiadiazole, benzothiazole, indole, benzotriazole, benzodioxolane, benzodioxane, carbazole, indole and quinazoline.

The term salt is understood to denote any form of the active constituent according to the invention in which this adopts an ionic form or is charged, and is coupled to a counter ion (a cation or anion) or is present in solution. The term is also understood to include complexes of the active constituent with other molecules and ions, in particular complexes that are complexed via ionic interactions. In particular the term is understood to denote (and this is also a preferred embodiment of the invention) physiologically compatible salts, in particular physiologically compatible salts with cations or bases and physiologically compatible salts with anions or acids or also a salt formed with a physiologically compatible acid or a physiologically compatible cation.

The term physiologically compatible is understood to mean that the substance, in particular the salt as such, is compatible when used in humans or mammals, and therefore for example does not act in a non-physiological manner (e.g. is not toxic).

The term physiologically compatible salt with anions or acids is understood within the meaning of the present invention to denote salts of at least one of the compounds according to the invention—generally protonated, for example on the nitrogen atom—as cation with at least one anion, which are physiologically compatible, especially when used in humans and/or mammals. In particular the term is understood within the meaning of the present invention to denote the salt formed with a physiologically compatible acid, namely salts of the respective active constituent with inorganic or organic acids, which are physiologically compatible, especially when used in humans and/or mammals. Examples of physiologically compatible salts of specific acids are salts of the following: hydrochloric acid, hydrobromic acid, sulphuric acid, methanesulfonic acid, formic acid, acetic acid, oxalic acid, succinic acid, malic acid, tartaric acid, mandelic acid, fumaric acid, lactic acid, citric acid, glutamic acid, 1,1-dioxo-1,2-dihydro 1$\lambda^6$-benzo[3]isothiazol-3-one (saccharinic acid), monomethylsebacic acid, 5-oxo-proline, hexane-1-sulfonic acid, nicotinic acid, 2-, 3- or 4-aminobenzoic acid, 2,4,6-trimethylbenzoic acid, α-lipoic acid, acetylglycine, acetylsalicylic acid, hippuric acid and/or aspartic acid. The hydrochloride salt is particularly preferred.

The term salt formed with a physiologically compatible acid is understood within the meaning of the present invention to denote salts of the respective active constituent with inorganic or organic acids, which are physiologically compatible, especially when used in humans and/or mammals. The hydrochloride is particularly preferred. Examples of physiologically compatible acids include the following: hydrochloric acid, hydrobromic acid, sulphuric acid, methanesulfonic acid, formic acid, acetic acid, oxalic acid, succinic acid, tartaric acid, mandelic acid, fumaric acid, lactic acid, citric acid, glutamic acid, 1,1-dioxo-1,2-dihydro-1$\lambda^6$-benzo[3]isothiazol-3-one (saccharinic acid), monomethylsebacic acid, 5-oxo-proline, hexane-1-sulfonic acid, nicotinic acid, 2-, 3- or 4-aminobenzoic acid, 2,4,6-trimethylbenzoic acid, α-lipoic acid, acetylglycine, acetylsalicylic acid, hippuric acid and/or aspartic acid.

The term physiologically compatible salts with cations or bases is understood within the meaning of the present invention to denote salts of at least one of the compounds according to the invention—generally a (deprotonated) acid—as anion with at least one, preferably inorganic, cation, which are physiologically compatible, especially when used in humans and/or mammals. Particularly preferred are the salts of the alkali and alkaline earth metals, but also salts with $NH_4^+$, in particular however (mono) or (di) sodium, (mono) or (di) potassium, magnesium or calcium salts.

The term salt formed with a physiologically compatible cation is understood within the meaning of the present invention to denote salts of at least one of the respective compounds as anion with at least one inorganic cation, which are physiologically compatible, especially when used in humans and/or mammals. Particularly preferred are the salts of the alkali and alkaline earth metals, but also $NH_4^+$, in particular however (mono) or (di)sodium, (mono) or (di)potassium, magnesium or calcium salts.

The compounds used according to the invention and their preparation are in principle known from DE 44 26 245 A1 with regard to the 1-phenyl-3-dimethylaminopropane compounds according to the general Formula I. All compounds other than these specific compounds can easily be prepared by the person skilled in the art in a similar way to the synthesis pathways described there.

In a particularly preferred variant of this embodiment, with regard to the 1-phenyl-3-dimethylaminopropane compounds of the general Formula I used according to the invention where $R^3$=H, these are present in the form of the diastereomers with the relative configuration Ia

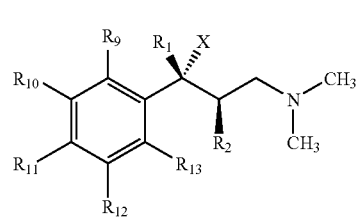

Ia in particular in mixtures with a larger proportion of this diastereomer compared to the other diastereomer, or are used as an isolated diastereomer.

It is particularly preferred if the 1-phenyl-3-dimethylaminopropane compound of Formula I used according to the invention is selected from the group consisting of:

(2RS,3RS)-1-dimethylamino-3-(3-methoxyphenyl)-2-methyl-pentan-3-ol,
(+)-(2R,3R)-1-dimethylamino-3-(3-methoxyphenyl)-2-methyl-pentan-3-ol,
(2R,3R)-1-dimethylamino-3-(3-methoxyphenyl)-2-methyl-pentan-3-ol,
(−)-(2S,3S)-1-dimethylamino-3-(3-methoxyphenyl)-2-methyl-pentan-3-ol,
(2S,3S)-1-dimethylamino-3-(3-methoxyphenyl)-2-methyl-pentan-3-ol,
(2RS,3RS)-3-(3,4-dichlorophenyl)-1-dimethylamino-2-methyl-pentan-3-ol,
(2RS,3RS)-3-(3-difluoromethylphenyl)-1-dimethylamino-2-methyl-pentan-3-ol,
(2RS,3RS)-1-dimethylamino-2-methyl-3-(3-methylsulfanylphenyl)-pentan-3-ol,
(3RS)-1-dimethylamino-3-(3-methoxyphenyl)-4,4-dimethylpentan-3-ol,
(2RS,3RS)-3-(3-dimethylamino-1-ethyl-1-hydroxy-2-methylpropyl)-phenol,
(1RS,2RS)-3-(3-dimethylamino-1-hydroxy-1,2-dimethylpropyl)-phenol,
(+)-(1R,2R)-3-(3-dimethylamino-1-hydroxy-1,2-dimethylpropyl)-phenol,
(1R,2R)-3-(3-dimethylamino-1-hydroxy-1,2-dimethylpropyl)phenol,
(−)-(1S,2S)-3-(3-dimethylamino-1-hydroxy-1,2-dimethylpropyl)-phenol,
(1S,2S)-3-(3-dimethylamino-1-hydroxy-1,2-dimethylpropyl)phenol,
(RS,RS)-3-(3-dimethylamino-1-ethyl-2-methylpropyl)phenol,
(−)-(1R,2R)-3-(3-dimethylamino-1-ethyl-2-methylpropyl)phenol,
(1R,2R)-3-(3-dimethylamino-1-ethyl-2-methylpropyl)phenol,
(+)-(1S,2S)-3-(3-dimethylamino-1-ethyl-2-methylpropyl)phenol,
(1S,2 S)-3-(3-dimethylamino-1-ethyl-2-methylpropyl)phenol,
(+)-(1R,2R)-acetic acid-3-dimethylamino-1-ethyl-1-(3-methoxy-phenyl)-2-methyl propyl ester,
(2RS,3RS)-3-(4-chlorophenyl)-1-dimethylamino-2-methyl-pentan-3-ol,
(+)-(2R,3R)-3-(3-dimethylamino-1-ethyl-1-hydroxy-2-methylpropyl)-phenol,
(2RS,3RS)-4-dimethylamino-2-(3-methoxyphenyl)-3-methylbutan-2-ol and
(+)-(2R,3R)-4-dimethylamino-2-(3-methoxyphenyl)-3-methylbutan-2-ol; and physiologically compatible salts thereof. Hydrochloride salts are preferred.

Particularly preferred substances include:
(RS,RS)-3-(3-dimethylamino-1-ethyl-2-methylpropyl)phenol,
(−)-(1R,2R)-3-(3-dimethylamino-1-ethyl-2-methylpropyl)phenol,
(1R,2R)-3-(3-dimethylamino-1-ethyl-2-methylpropyl)phenol,
(−)-(1S,2S)-3-(3-dimethylamino-1-ethyl-2-methylpropyl)phenol,
(1S,2S)-3-(3-dimethylamino-1-ethyl-2-methylpropyl)phenol, and physiologically compatible salts thereof.

Especially preferred compounds are:
(−)-(1R,2R)-3-(3-dimethylamino-1-ethyl-2-methyl-propyl)phenol,
(1R,2R)-3-(3-Dimethylamino-1-ethyl-2-methylpropyl)phenol, or physiologically compatible salts thereof.

The pharmaceutical compositions of the invention, which comprise one or more of the aforementioned compounds according to the invention, are useful for treating neuropathic pain, preferably mono- and/or polyneuropathic pain, particularly preferably polyneuropathic pain, furthermore preferably diabetic neuropathic pain, more preferably diabetic peripheral neuropathic pain, and in addition preferably for treating diabetic neuropathy, and particularly preferably for treating diabetic peripheral neuropathy. In accordance with the invention the compositions contain at least one aforementioned active constituent used according to the invention, as well as optionally suitable additives and/or auxiliary substances.

Suitable additives and/or auxiliary substances within the scope of the present invention include all substances known to persons skilled in the art for producing galenical formulations. The selection of these auxiliary substances as well as the amounts to be used depend on whether the medicament is to be administered orally, intravenously, intraperitonealy, intradermally, intramuscularly, intranasally, buccally or topically. For oral administration, suitable preparations may take the form of tablets, chewable tablets, coated pills, capsules, granules, drops, juices or syrups, while for parenteral, topical and inhalative administration, suitable preparations may be formulated as solutions, suspensions, readily reconstitutable dry preparations as well as sprays. A further possible form is as suppositories for rectal administration. Examples of percutaneous administration forms include use in a depot in dissolved form, in a carrier film or a plaster, optionally with the addition of agents promoting penetration of the skin.

Examples of auxiliary substances and additives for oral administration forms include disintegrants, lubricants, binders, fillers, mold release agents, optionally solvents, taste enhancers, sugars, in particular carriers, diluents, colorants, antioxidants, etc. For suppositories there may be used inter alia waxes or fatty acid esters, and for parenteral application agents there may be used carriers, preservatives, suspension aids, etc. The compounds according to the invention may be released in a delayed manner from orally, rectally or percutaneously usable preparation forms. In the medical indications for use according to the invention corresponding Retard formulations, in particular in the form of a "once daily" preparation, which need to be taken only once a day, are especially preferred for use in treating many medical indications for which the active substances of the invention are suitable.

The amounts of active constituent to be administered to patients vary depending on the patient's weight, type of application, and the severity of the medical condition. Preferred are medicaments that contain at least 0.05 to 90.0% of the active constituent, in particular low active dosages, in order to avoid side effects. Normally 0.1 to 5000 mg/kg, in particular 1 to 500 mg/kg and preferably 2 to 250 mg/kg of body weight of at least one compound used according to the invention are administered. However, the administration of 0.01-5 mg/kg, preferably 0.03 to 2 mg/kg and especially 0.05 to 1 mg/kg of body weight is also preferred and customary.

Examples of suitable auxiliary substances for inclusion in the pharmaceutical compositions according to the invention include water, ethanol, 2-propanol, glycerol, ethylene glycol, propylene glycol, polyethylene glycol, polypropylene glycol, glucose, fructose, lactose, sucrose, dextrose, molasses, starch, modified starch, gelatin, sorbitol, inositol, mannitol, microcrystalline cellulose, methylcellulose, carboxymethylcellulose, cellulose acetate, shellac, cetyl alcohol, polyvinylpyrrolidone, paraffins, waxes, natural and synthetic gums, acacia gum, alginates, dextran, saturated and unsaturated fatty acids, stearic acid, magnesium stearate, zinc stearate, glyceryl stearate, sodium lauryl sulfate, edible oils, sesame oil, coconut oil, ground nut oil, soya bean oil, lecithin, sodium lactate, polyoxyethylene and polyoxypropylene fatty acid esters, sorbitan fatty acid esters, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulphate, zinc sulphate, calcium sulphate, potassium carbonate, calcium phosphate, dicalcium phosphate, potassium bromide, potassium iodide, talcum, kaolin, pectin, crospovidone, agar and bentonite.

Medicaments and pharmaceutical compositions according to the invention may be prepared using agents, equipment, methods and processes known in the prior art for producing pharmaceutical formulations, such as are described, for example, in "Remington's Pharmaceutical Sciences", edited by A. R. Gennaro, 17th Ed., Mack Publishing Company, Easton, Pa. (1985), in particular in Part 8, Chapters 76 to 93.

Thus, for example, for a solid formulation such as a tablet, the active constituent of the medicament can be granulated with a pharmaceutical carrier, for example conventional tablet constituents such as maize starch, lactose, sucrose, sorbitol, talcum, magnesium stearate, dicalcium phosphate or pharmaceutically acceptable gums, and pharmaceutical diluents, such as for example water, in order to form a solid composition that contains the active constituent in homogeneous distribution. A homogeneous distribution is understood here to mean that the active constituent is distributed uniformly over the whole composition, so that the latter can be subdivided without any problem into identically active unit dose forms such as tablets, pills or capsules. The solid composition is then subdivided into unit dose forms. The tablets or pills of the medicament according to the invention or of the compositions according to the invention can also be coated or compounded in some other way so as to produce a dose form having delayed release. Suitable coating agents are inter alia polymeric acids and mixtures of polymeric acids with materials such as for example schellac, cetyl alcohol and/or cellulose acetate.

Even if the medicaments prepared according to the invention exhibit only slight side effects, it can for example be advantageous, in order to avoid certain forms of dependence, to employ apart from the aforementioned compound according to the invention also morphine antagonists, in particular naloxone, naltrexone and/or levallorphan. In tests it was found for example for morphine and compound 10 (see Example 0 hereinafter) that the substances are also effective with naloxone in treating neuropathic pain.

The invention also relates to a method for treating neuropathic pain, for treating neuropathic, preferably mononeuropathic and/or polyneuropathic pain, particularly preferably polyneuropathic pain, and in addition preferably for treating diabetic neuropathic pain, preferably diabetic peripheral neuropathic pain, and in addition preferably for treating diabetic neuropathy, particularly preferably diabetic peripheral neuropathy, in which at least one of the aforementioned compounds is used according to the invention.

The following examples are intended to describe the invention in more detail, without however restricting the subject-matter of the invention.

EXAMPLES

Example 0

Tested Substances

The following compounds were tested and are hereinafter correspondingly abbreviated as compound (or Comp.) 1, etc. in Table 1:

TABLE 1

| Name: | Compound |
|---|---|
| (2RS,3RS)-1-dimethylamino-3-(3-methoxyphenyl)-2-methylpentan-3-ol; hydrochloride | 1 |
| (2S,3S)-1-dimethylamino-3-(3-methoxyphenyl)-2-methylpentan-3-ol; hydrochloride | 2 |
| (2R,3R)-1-dimethylamino-3-(3-methoxyphenyl)-2-methylpentan-3-ol; hydrochloride | 3 |
| (1RS,2RS)-3-(3-dimethylamino-1-hydroxy-1,2-dimethylpropyl)-phenol; hydrochloride | 5 |
| (1S,2S)-3-(3-dimethylamino-1-hydroxy-1,2-dimethylpropyl)phenol; hydrochloride | 6 |
| (1R,2R)-3-(3-dimethylamino-1-hydroxy-1,2-dimethylpropyl)phenol; hydrochloride | 7 |
| (2RS,3RS)-3-(difluoromethylphenyl)-1-dimethylamino-2-methylpentan-3-ol; hydrochloride | 8 |
| (1R,2R)-3-(3-dimethylamino-1-ethyl-2-methyl-propyl)-phenol; hydrochloride | 9 |
| (1S,2S)-3-(3-dimethylamino-1-ethyl-2-methyl-propyl)phenol; hydrochloride | 10 |
| 3-(3-dimethylamino-1,2-dimethylpropenyl)-phenol; hydrochloride | 14 |

Additionally:
Morphine Mor
Gabapentin GBP

Example 1

Bennett

Neuropathic Pain in Rats

The effectiveness in treating neuropathic pain was investigated in the Bennett model (chronic constriction injury; Bennett and Xie, 1988, Pain 33: 87-107).

Sprague-Dawley rats weighing 140-160 g are provided with four loose ligatures of the right sciatic nerve under nembutal narcosis. The animals develop a hypersensitivity in the paw innervated by the damaged nerve, which after a healing phase of one week is quantified over about four weeks by means of a 4° C. cold metal plate (cold allodynia). The animals are observed for two minutes on this plate and the number of retractive movements of the damaged paw are measured. The effect of the substance is determined with reference to the base value before application of the substance, at four different times over a period of one hour (15, 30, 45 and 60 minutes after application) and the resultant area under the curve (AUD) as well as the inhibition of cold allodynia at the individual measurement points is expressed in percent effect with reference to the vehicle control (AUD) and to the initial value (individual measurement points). The cohort size is n=10.

The results are summarized together with those from Example 2 in the following Table 2.

Example 2

Chung

In Vivo Experiments According to Chung

Spinal nerve ligatures according to Kim & Chung (1992 Pain 50, 355-363) were applied to the left L5/L6 spinal nerves of male Spraque-Dawley rats. Four to six days after the operation the tactile threshold baseline (withdrawal threshold) was measured on the ipsilateral and contralateral rear paw by an electronic von Frey anaesthesiometer (IITC Life Science, USA). After the test and measurement of the baseline, morphine, gabapentin and some of the aforementioned compounds used according to the invention were administered. The tactile withdrawal thresholds were measured 30 minutes after the administration. The results are expressed as ED50 and % maximal possible effect (% MPE) on the ipsilateral side, in which the baseline is taken as 0% and the withdrawal threshold of a control group is taken as 100% MPE.

The results together with those from Example 1 are summarized in Table 2:

TABLE 2

Testing of the inhibition of neuropathic pain in rats after intraperitoneal (i.p.) or per oral (p.o.) administration

| Compound | Cold allodynia ED50 mg/kg i.p. (95% confidence region) [band width of the measurement values] | Tactile allodynia ED50 mg/kg i.p. (95% confidence region) [band width of the measurement values] |
|---|---|---|
| Morphine | 7.1 [5.7-9.4] | 4.6 [3.8-5.7] |
| Gabapentin | 214 (p.o.) | 92.6 |
| 1 | 11.1 [9.9-12.3] | 10.1 |
| 2 | 26.0 | — |
| 3 | 9.2 | — |
| 5 | 15.0 | — |
| 6 | 32.6 | 4.65 |
| 7 | 11.1 | — |
| 8 | 17.1 | — |
| 9 | 13 | 8.15 [3.8-14.5] |
| 10 | 1.2 [0.6-3.1] | 1.5 [0.74-12.54] |
| 14 | 3.6 | — |

The compounds all show a marked and dose-dependent inhibition of cold allodynia in Bennett animals and of tactile allodynia in Chung animals. Moreover, in Chung animals in some cases a surprisingly long action duration of up to 30 hours after i.p. application is observed.

Example 3

In Vivo Experiments in Rats with Diabetic Neuropathy

Male Sprague-Dawley rats weighing 160-180 g received an intra-peritoneal injection of streptozotocin (75 mg/kg body weight) dissolved in pH 4.6 citrate buffer. One week later diabetic animals were identified by measuring the blood glucose level, and those with a blood glucose level of $\geq 17$ mM were included in the study. Three and four weeks after administration of streptozotocin the mechanical reaction threshold was measured in diabetic animals by the method of Randall and Sellito (1957 Arch. Int. Pharmacody. 61:409-419) before (pre-test) and at various times after administration of the test substance or vehicle (post-test). Diabetic animals exhibit a reduced mechanical reaction threshold and thus a mechanical hyperalgesia compared to control animals that had simultaneously received vehicle solution instead of streptozotocin. The maximum pressure exerted on the rear paw was 250 g. The end point of the mechanical reaction threshold in grams was determined based on the reaction of the animal (withdrawal of the rear paw, vocalisation or evasive reaction). The size of the cohort in the individual dose stages was n=10. The maximum possible response in percent (% MPE=% of maximum possible effect) was calculated according to the formula:

$$\% \text{ MPE} = (\text{post-test} - \text{pre-test})/(250 - \text{pre-test}) \times 100.$$

ED50 values (dose at which 50% maximum inhibition occurred) were determined by regression analysis from the % MPE values at the time of the maximum effect.

TABLE 3

Investigation of the inhibition of diabetic neuropathic pain in rats after intraperitoneal (i.p.) substance administration

| Compound | Mechanical hyperalgesia ED50 mg/kg i.p. (95% confidence region) | Mechanical hyperalgesia Maximum effect in % MPE at (dose mg/kg i.p.) |
|---|---|---|
| Morphine | 3.0 (1.8-4.0) | 89% (10 mg/kg) |
| Gabapentin | 225 (186-274) | 80% (464 mg/kg) |
| Tramadol | 9.2 (7.0-11.8) | 86% (21.5 mg/kg) |
| Compound 9 | 8.9 (7.1-11.1) | 100% (31.6 mg/kg) |

Of the tested compounds, compound 9 achieved the highest maximum effect.

Example 4

Tolerance to Morphine

The underlying question is the action of a test substance having a presumably opioid action mechanism in patients who are tolerant or treatment-resistant to morphine. In Bennett animals (according to Example 1) that have developed a tolerance to morphine, the tested compounds still exhibited a significant anti-allodynic action. The action of test substances in naïve (non-morphine-tolerant) animals and morphine-tolerant animals is compared in Table 4. Morphine (Mor) understandably no longer exhibits any effect, whereas the other tested compounds produce a marked inhibition of cold allodynia in these animals. Morphine [10 mg/kg i.p.], Compound 9 [10 and 21.5 mg/kg i.p.], Compound 10 [0.46 and 1 mg/kg i.p.], Compound 4 [21.5 mg/kg i.p.] and Compound 11 [21.5 mg/kg i.p.] were tested analogously to Example 1.

TABLE 4

Examination of the inhibition of neuropathic pain in rats after intraperitoneal (i.p.) substance administration to naïve and morphine-tolerant animals in % AUD.

| Compound [dose mg/kg i.p.] | Cold allodynia (% AUD) Morphine-tolerant animals | Cold allodynia (% AUD) Naïve animals |
|---|---|---|
| Morphine [10] | −22.0 | 78.6 |
| 9 [10] | 37.3 | 49.3 |
| 9 [21.5] | 36.7 | 53.4 |
| 10 [0.46] | 22.9 | 29.0 |
| 10 [1] | 39.9 | 42.7 |
| 10 [2.15] | 13.0 | 59.2 |
| 4 [21.5] | 75.2 | 65.5 |
| 11 [21.5] | 42.6 | 69.2 |

Example 5

Parenteral Application Form 20 g of Compound 9 are dissolved in 1 liter of water for injection at room temperature and then adjusted by addition of NaCl to isotonic conditions.

Example 6

Comparison of Mononeuropathic and Polyneuropathic Pain

Experimental Procedure

Male Sprague Dawley rats (140-180 g, Janvier, France) are kept under standard conditions (06.00-18.00 hours light, 18.00-06.00 hours darkness; 20°-24° C. room temperature; 35-70% relative atmospheric humidity, tap water and standard feed as desired) in groups of five animals in Macrolon type 4 cages.

Mononeuropathy (Spinal Nerve Ligature, SNL)

Under pentobarbital narcosis (Narcoren, 60 mg/kg i.p., Merial GmbH, Germany) the spinal nerves L5 and L6 are tightly bound unilaterally on the left side with a silk thread (NC silk black, USP 5/0, metric 1, Braun Melsungen AG, Germany) (Kim and Chung, Pain 1992; 50: 355-63). After the operation the animals were allowed to recover for one week and within this time developed a hypersensitivity on the ipsilateral (left) paw. The hypersensitivity to a pressure stimulus can be measured using an electronic von Frey filament (Somedic, Sweden). For this purpose the animals are placed on a grating under a hood. After the animals became accustomed to the surroundings the damaged (ipsilateral, left) and undamaged (contralateral, right) rear paws are subjected to increasing pressure on the underside of the paw until the animal tries to retract the corresponding paw. The median value of five tests defines the withdrawal threshold of a test time point. The animals are tested on both rear paws before and at various times after administration of the substance or vehicle. For each animal the difference between the test value and pre-test for the ipsilateral and contralateral side is determined, and the result is expressed as the mean value (MW) and standard error of the mean (SEM) for the groups consisting in each case of 10 animals. The difference between the mean difference values of the ipsilateral and contralateral side defines the hypersensitivity induced by mononeuropathy. The statistical significance of the effect of a substance is determined on the basis of the difference values compared to the vehicle group for the ipsilateral and contralateral side, by means of bifactorial variance analysis and post hoc analysis according to Bonferroni.

Polyneuropathy (Streptozotocin-Induced Diabetic Neuropathy, STZ)

Rats receive a single i.p. dose of Streptozotocin (STZ, Sigma Aldrich Chemie, Germany) or vehicle (0.1 mM citrate buffer, pH 4.6). After one week the blood sugar values are determined and animals treated with STZ that have a blood sugar value of $\geq 17$ mM are classed as diabetic in the experiment. Diabetic animals develop a hypersensitivity in the rear paws. The hypersensitivity to a pressure stimulus can be measured using a pressure pain instrument (algesiometer; Ugo Basile, Italy) according to the method of Randall and Selitto (Arch. Int. Pharmcodyn. 1957; 111: 409-19) in diabetic animals compared to healthy control animals of the same weight, in the third week after STZ treatment. After the animals had become accustomed to the surroundings, the rear right paw of damaged (diabetic) and undamaged (healthy) animals was subjected to increasing pressure on the upper side of the paw until the corresponding paw is withdrawn or the animal gives a vocal response. This value defines the withdrawal threshold of a test time point. Diabetic and healthy animals are tested before and at various times after administration of the substance or vehicle. For each animal the difference between the test value and pre-test is determined, and for the groups, each consisting of ten animals, the result is expressed as the mean value (MW) and standard error of the mean (SEM). The difference between the mean difference values of the diabetic and healthy animals defines the polyneuropathy-induced hypersensitivity. The statistical significance of the effect of a substance is determined on the basis of the difference values with respect to the vehicle group for diabetic and healthy animals by means of bifactorial variance analysis and post hoc analysis according to Bonferroni.

Results

Mononeuropathic Pain (1R,2R)-3-(3-dimethylamino-1-ethyl-2-methyl-propyl)-phenol hydrochloride 9 (0.1-10 mg/kg, i.v., Table 1) shows a dose-dependent increase of the withdrawal threshold on the ipsilateral rear paw. The statistically significant minimal effective dose is 1 mg/kg. The mean difference value between the ipsilateral withdrawal threshold of healthy control animals and the ipsilateral withdrawal threshold of mononeuropathic animals in this series of experiments is 36 g. Complete inhibition of the mononeuropathically-induced withdrawal threshold reduction is thus achieved at values (test value−retest value) of $\geq 36$ g on the ipsilateral side. Time points at which this value is reached or exceeded are given in bold type in boxes in the table. Contralateral measurement values are not included in this analysis. In the highest dosage group of 10 mg/kg i.v. full inhibition of the mononeuropathically-induced withdrawal threshold reduction is reached after 30 minutes. The contralateral withdrawal threshold is also raised in a dose-dependent manner. The statistically significant minimal effective dose is 10 mg/kg.

TABLE 1

(1R,2R)-3-(3-dimethylamino-1-ethyl-2-methyl-propyl)-phenol hydrochloride (9) mononeuropathy

| Dose (mg/kg, i.v.) | Side | | 30 min | 60 min | 180 min |
|---|---|---|---|---|---|
| Vehicle | Ipsi | MW | 0.70 | 0.06 | -1.33 |
| | | SEM | 1.16 | 1.31 | 1.09 |
| | | Significance | n.s. | n.s. | n.s. |
| | Contra | MW | -4.06 | 0.83 | -3.79 |
| | | SEM | 2.63 | 3.77 | 2.90 |
| | | Significance | n.s. | n.s. | n.s. |
| 0.1 | Ipsi | MW | 1.74 | -0.59 | -2.24 |
| | | SEM | 1.55 | 1.44 | 1.15 |
| | | Significance | n.s. | n.s. | n.s. |
| | Contra | MW | 0.06 | -3.13 | -4.30 |
| | | SEM | 4.52 | 4.12 | 3.01 |
| | | Significance | n.s. | n.s. | n.s. |
| 0.316 | Ipsi | MW | 5.78 | 2.21 | 1.68 |
| | | SEM | 2.34 | 2.93 | 1.41 |
| | | Significance | n.s. | n.s. | n.s. |
| | Contra | MW | 0.39 | -6.20 | 2.21 |
| | | SEM | 4.71 | 3.03 | 3.81 |
| | | Significance | n.s. | n.s. | n.s. |
| 1 | Ipsi | MW | 12.86 | 7.09 | 2.01 |
| | | SEM | 2.42 | 0.80 | 0.64 |
| | | Significance | * | n.s. | n.s. |
| | Contra | MW | 2.90 | 2.45 | -6.65 |
| | | SEM | 3.32 | 3.92 | 2.45 |
| | | Significance | n.s. | n.s. | n.s. |
| 3.16 | Ipsi | MW | 18.43 | 20.32 | 11.06 |
| | | SEM | 2.90 | 2.39 | 1.45 |
| | | Significance | * | * | * |
| | Contra | MW | 8.02 | 2.85 | -0.34 |
| | | SEM | 4.13 | 3.09 | 3.81 |
| | | Significance | n.s. | n.s. | n.s. |
| 10 | Ipsi | MW | 42.05 | 19.47 | 13.65 |
| | | SEM | 3.50 | 1.52 | 1.40 |
| | | Significance | * | * | * |
| | Contra | MW | 31.85 | 10.62 | 4.51 |
| | | SEM | 3.23 | 4.92 | 4.17 |
| | | Significance | * | n.s. | n.s. |

(test value − pre-test value (g); * $p < 0.05$ with respect to vehicle; n.s. = not significant with respect to vehicle)

Polyneuropathic Pain (1R,2R)-3-(3-dimethylamino-1-ethyl-2-methyl-propyl) hydrochloride 9 (0.1-1 mg/kg, i.v., Table 2) shows a dose-dependent increase of the withdrawal threshold in the rear paw of diabetic rats. The statistically significant minimal effective dose is 0.3 mg/kg. The mean difference value between the withdrawal threshold of naive control animals and the withdrawal threshold of polyneuropathic animals is in this series of experiments 43 g. Complete inhibition of the polyneuropathically-induced withdrawal threshold reduction is thus achieved at values (test value−pre-test value) of ≧43 g in diabetic animals. Time points at which this value is reached or exceeded are shown in grey in the table. Measurement values of naive animals are not included in this analysis. In the highest dosage group of 1 mg/kg i.v. complete inhibition of the polyneuropathically-induced withdrawal threshold reduction is reached after 15 minutes and 30 minutes. The withdrawal threshold of healthy control animals is also raised in a dose-dependent manner. The statistically significant minimal effective dose is 1 mg/kg.

TABLE 2

(1R, 2R)-3-(3-dimethylamino-1-ethyl-2-methyl-propyl) hydrochloride (9) polyneuropathy

| Dose (mg/kg, i.v.) | Group | | 15 min | 30 min | 45 min | 60 min |
|---|---|---|---|---|---|---|
| 0.1 | Diabetes | MW | 1.0 | -2.0 | 6.0 | -2.0 |
| | | SEM | 6.4 | 5.5 | 3.4 | 5.5 |
| Vehicle | | MW | 3.0 | 2.0 | -11.0 | 0.0 |
| | | SEM | 4.2 | 3.6 | 3.5 | 3.7 |
| | | Significance | n.s. | n.s. | n.s. | n.s. |
| 0.1 | Naive | MW | 4.0 | -12.0 | -2.0 | -5.0 |
| | | SEM | 4.8 | 7.7 | 5.3 | 6.2 |
| Vehicle | | MW | -9.0 | -2.0 | -5.0 | -3.0 |
| | | SEM | 4.8 | 5.1 | 4.5 | 2.1 |
| | | Significance | n.s. | n.s. | n.s. | n.s. |
| 0.316 | Diabetes | MW | 35.0 | 30.0 | 24.0 | 16.0 |
| | | SEM | 9.2 | 6.3 | 6.9 | 4.8 |
| Vehicle | | MW | -6.0 | -5.0 | 0.0 | 1.0 |
| | | SEM | 3.7 | 6.7 | 6.0 | 3.5 |
| | | Significance | * | * | * | n.s. |
| 0.316 | Naive | MW | 17.0 | -5.0 | -5.0 | 2.0 |
| | | SEM | 3.3 | 7.3 | 4.5 | 2.5 |
| Vehicle | | MW | -6.0 | -5.0 | -14.0 | 2.0 |
| | | SEM | 6.7 | 5.8 | 6.7 | 4.4 |
| | | Significance | n.s. | n.s. | n.s. | n.s. |
| 1 | Diabetes | MW | 54.0 | 49.0 | 34.0 | 27.0 |
| | | SEM | 10.8 | 8.7 | 6.5 | 6.2 |
| Vehicle | | MW | 1.0 | -10.0 | 4.0 | 4.0 |
| | | SEM | 5.9 | 3.3 | 6.4 | 3.4 |
| | | Significance | * | * | * | * |
| 1 | Naive | MW | 42.0 | 28.0 | -2.0 | 7.0 |
| | | SEM | 7.6 | 7.4 | 6.3 | 4.5 |
| Vehicle | | MW | -4.0 | -5.0 | -15.0 | -2.0 |
| | | SEM | 5.6 | 8.7 | 3.1 | 3.6 |
| | | Significance | * | * | n.s. | n.s. |

(test value − pre-test value (g); * $p < 0.05$ with respect to vehicle; n.s. not significant with respect to vehicle)

1R,2R)-3-(3-dimethylamino-1-ethyl-2-methyl-propyl)-phenol hydrochloride 9 produces a dose-dependent increase of the pressure-mediated withdrawal threshold in mononeuropathic and polyneuropathic pain. In both pain models (1R,2R)-3-(3-dimethylamino-1-ethyl-2-methyl-propyl)-phenol produces a selective inhibition of the pathologically induced pain response, without at the same time influencing the normal pain response. A clear difference is found in the level of effectiveness of (1R,2R)-3-(3-dimethylamino-1- ethyl-2-methyl-propyl)-phenol in both models. Whereas in the polyneuropathic pain model a significant inhibition is already detectable at 0.316 mg/kg i.v., a significant inhibition in the mononeuropathic pain model occurs only at 1 mg/kg i.v., i.e. at a three times higher dosage. A similar behavior is observed at the dosage at which the maximum effect is achieved. In the polyneuropathic pain model complete inhibition is reached at 1 mg/kg i.v., whereas in the mononeuropathic pain model complete inhibition is reached only at 10 mg/kg i.v., i.e. at a ten times higher dosage. These data show that 1R,2R)-3-(3-dimethylamino-1-ethyl-2-methyl-propyl)-phenol is particularly suitable for the treatment of polyneuropathic pain states.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A method of treating polyneuropathic pain in a subject suffering therefrom, said method comprising administering to said subject an effective polyneuropathic pain inhibiting amount of (1R,2R)-3-(3-dimethylamino-1-ethyl-2-methyl-propyl)phenol
or a pharmaceutically acceptable salt thereof.

2. A method according to claim 1, comprising administering a hydrochloride salt of (1R,2R)-3-(3-dimethylamino-1-ethyl-2-methylpropyl)phenol.

3. A method according to claim 1, wherein said polyneuropathic pain is diabetic polyneuropathic pain.

4. A method according to claim 1, wherein said polyneuropathic pain is peripheral polyneuropathic pain.

5. A method according to claim 1, wherein said polyneuropathic pain is peripheral diabetic polyneuropathic pain.

6. A method of treating diabetic polyneuropathy in a subject suffering therefrom, said method comprising administering to said subject a pharmacologically effective amount of (1R,2R)-3-(3-dimethylamino-1-ethyl-2-methylpropyl)phenol
or a pharmaceutically acceptable salt thereof.

* * * * *